(12) United States Patent
Roewer et al.

(10) Patent No.: US 9,125,953 B2
(45) Date of Patent: Sep. 8, 2015

(54) HALOGENATED ETHER COMPLEX

(75) Inventors: Norbert Roewer, Wurzburg (DE); Jens Broscheit, Wurzburg (DE)

(73) Assignee: SAPIOTEC GMBH, Wurzburg (DE)

(*) Notice: Subject to any disclaimer, the term of this patent is extended or adjusted under 35 U.S.C. 154(b) by 552 days.

(21) Appl. No.: 13/522,109

(22) PCT Filed: Jan. 14, 2011

(86) PCT No.: PCT/EP2011/050428
§ 371 (c)(1),
(2), (4) Date: Jul. 13, 2012

(87) PCT Pub. No.: WO2011/086146
PCT Pub. Date: Jul. 21, 2011

(65) Prior Publication Data
US 2012/0296077 A1 Nov. 22, 2012

(30) Foreign Application Priority Data
Jan. 14, 2010 (EP) .................................. 10150786

(51) Int. Cl.
| | | |
|---|---|---|
| C08B 30/18 | (2006.01) | |
| C08B 37/16 | (2006.01) | |
| A01N 43/04 | (2006.01) | |
| A61K 31/715 | (2006.01) | |
| A61K 47/48 | (2006.01) | |
| A61K 9/00 | (2006.01) | |
| A61K 31/08 | (2006.01) | |
| B82Y 5/00 | (2011.01) | |
| A61K 47/40 | (2006.01) | |

(52) U.S. Cl.
CPC ......... *A61K 47/48969* (2013.01); *A61K 9/0019* (2013.01); *A61K 31/08* (2013.01); *B82Y 5/00* (2013.01); *C08B 37/0015* (2013.01); *A61K 47/40* (2013.01)

(58) Field of Classification Search
CPC ............... A61K 9/0019; A61K 31/08; A61K 47/48969; A61K 47/40; C08B 37/0015
USPC ............................................. 536/46; 514/58
See application file for complete search history.

(56) References Cited

U.S. PATENT DOCUMENTS

| | | |
|---|---|---|
| 3,216,897 A | 11/1965 | Krantz et al. |
| 4,725,442 A | 2/1988 | Haynes |

FOREIGN PATENT DOCUMENTS

| | | |
|---|---|---|
| GB | 2350297 | 11/2000 |
| WO | 2008070490 | 6/2008 |

OTHER PUBLICATIONS

Brewster and Loftsson, "Cyclodextrins as pharmaceutical solubilizers," Adv Drug Delivery Rev, 2007, 59:645-666.
Viernstein et al., "Intravenous anaesthesia with isoflurane in the rabbit," Pharm Pharmacol Lett, 1994, 3:165-168.
English Translation of the International Preliminary Report on Patentability (Chapter I) for International Application PCT/EP2011/050428, mailed Aug. 16, 2012, 8 pages.

*Primary Examiner* — Scarlett Goon
(74) *Attorney, Agent, or Firm* — Casimir Jones S.C.

(57) ABSTRACT

The invention relates to a complex made of α-cyclodextrin and a halogenated ether, characterized by a content of the halogenated ether of at least 3 wt % of the total weight of the complex.

17 Claims, No Drawings

HALOGENATED ETHER COMPLEX

The present invention is a §371 U.S. National Entry of International Patent Application PCT/EP2011/050428, filed Jan. 14, 2011, which is incorporated herein by reference, and which claims priority benefit of European Patent Application 10150786.1, filed Jan. 14, 2010.

The invention relates to a flurane complex and to the formulation thereof as an anesthetic.

Fluranes are medicaments which are used in anesthesia for maintaining or inducing narcosis and are ingested by inhalation in the prior art. Inhalation anesthetics are administered as gases, or liquids vaporized by means of a vaporizer, via a respiratory mask, a laryngeal mask or an endotracheal tube.

Fluranes have a low boiling point and a high vapor level. They are polyhalogenated ethers. They are lipophilic substances whose anesthetic efficacy is explained inter alia by a nonspecific interaction, caused by lipophilicity, with constituents of the cell membrane.

It is an object of the invention to provide a flurane formulation which permits the administration thereof by a route other than inhalation.

The invention provides a complex formed from α-cyclodextrin and a flurane, in which the flurane content is at least 3% by weight of the total weight of the complex.

The invention has recognized that, surprisingly, it is possible to prepare complexes of fluranes with α-cyclodextrin, which can form the basis for a formulation of these anesthetics for oral or intravenous administration and can have a high flurane content of 3 or more % by weight.

Cyclodextrins generally have a toroid form and have a correspondingly shaped cavity. The fluranes enter this cavity as a guest molecule, such that a complex of the extremely lipophilic fluranes which can be formulated as an aqueous solution and which can provide the fluranes at the intended site of pharmaceutical action is obtained.

α-Cyclodextrin has six glucopyranose units, each of which bears three OH groups which may optionally be substituted (for example methylated).

The flurane content of the inventive complex is preferably at least 5% by weight, more preferably at least 7% by weight, more preferably at least 8% by weight, more preferably 8 to 12% by weight. The values mentioned can be combined as desired to give inventive ranges.

The flurane is a polyfluorinated ether and is preferably selected from the group consisting of sevoflurane, enflurane, isoflurane, desflurane and methoxyflurane. Sevoflurane is particularly preferred.

According to the invention, the complex may have a water content (residual water content) of 5 to 15% by weight, preferably 7 to 13% by weight.

The invention further provides an inventive complex for use as a medicament.

The invention further provides an anesthetic which has been formulated for oral and/or intravenous administration and comprises an inventive complex.

The invention further provides a process for producing an inventive complex, comprising the steps of
 a) preparing an aqueous solution of α-cyclodextrin,
 b) adding the flurane to the aqueous solution,
 c) removing the precipitated complex.

According to the invention, an aqueous solution of α-cyclodextrin is prepared in the first step. This is preferably a full solution in which no undissolved cyclodextrin remains in suspension. Preferred concentrations of α-cyclodextrin in the aqueous solution are 5 to 30% by weight, preferably 5 to 20% by weight, more preferably 5 to 15% by weight. If unsubstituted α-cyclodextrin is used, the upper limit is 14.5% by weight (solubility of unsubstituted α-cyclodextrin in water). Substituted, especially (partly) methylated, α-cyclodextrins may have a higher solubility in water.

The α-cyclodextrin is preferably dissolved in water at room temperature. The flurane is added to the dissolved α-cyclodextrin. A complex forms, which precipitates out of the aqueous solution in crystalline form and can be removed.

In the context of the invention, it is preferable when the flurane is added in a molar ratio relative to α-cyclodextrin of 1:0.5 to 1:2, preferably 1:0.8 to 1:1.2. More particularly, an approximately equimolar addition of the flurane can be effected in relation to the cyclodextrin.

In the precipitated complex, a molar ratio of flurane to the cyclodextrin, for instance, in the range of 1:1.5 to 1:6 is found. Preference is given to ranges from 1:1.5 to 1:2. Measured by the molar ratio of flurane and cyclodextrin in the precipitated complex, preference is thus given to using a molar excess of the flurane in the production.

According to the invention, addition of the flurane is preferably followed by cooling, for example to a temperature of 5 to 10° C., in order to promote the precipitation of the complex and hence to increase the yield.

Working examples and comparative examples are described hereinafter.

1. Materials Used
 purified water (Millipore Q quality water)
 α-cyclodextrin
 β-cyclodextrin
 2-hydroxypropyl-β-cyclodextrin
 methyl-β-cyclodextrin (RAMEB)
 sevoflurane All cyclodextrins were purchased from Cyclo Lab Cyclodextrin Research & Development Laboratory Ltd., Hungary. Sevoflurane was purchased from Abbott GmbH, Wiesbaden.

2. Determination of the Sevoflurane Content of Complexes Produced

The sevoflurane content of the complexes was determined by gas chromatography. The gas chromatography conditions were as follows:

| | |
|---|---|
| Gas chromatograph: | Shimadzu GC-17A |
| Detector: | Flame ionization detector (FID) |
| Injector: | Shimadzu AoC-5000 auto injector |
| Software: | Shimadzu Class-VP 7.4 version |
| Gases: | |
| Carrier: | helium (99.999%) |
| further gases: | nitrogen (99.999%) |
| | synthetic air (99.999%) |
| | hydrogen (Whatman hydrogen generator) |
| Column: | Rtx624 (30 m × 0.32 mm × 1.8 mm) (Restek) |

Temperature Program:

| Rate (° C./min) | Temperature (° C.): | Time (min): |
|---|---|---|
| — | 38 | 4.0 |
| 40 | 220 | 1.5 |

| | |
|---|---|
| Injector temperature: | 220° C. |
| Detector temperature: | 220° C. |
| Split ratio: | 100:1 |
| Flow rate: | 30 cm/s |

The injection program was as follows: after an incubation time of 10 minutes at 60° C., a vapor sample with a volume of 250 µl at 70° C. was injected into the gas chromatograph.

Sample Preparation

Comparative solutions: 1 ml of distilled water containing 250 µl of DMF is introduced into the vials.

Calibration solutions: as a stock solution, 100 mg of sevoflurane are weighed into 2 ml glass bottles and filled up to the mark with DMF.

Various amounts of this stock solution (20, 65, 110, 155 and 200 µl) are each made up to 200 µl with DMF and introduced into headspace vials (19.5 ml) together with 1 ml of distilled water.

Sample solution: 50 mg of the sample solution are introduced into a headspace vial (19.5 ml) together with 1 ml of distilled water and 200 µl of DMF. In addition, 1 ml of mother solution (prepared from the supernatant of the complexation of sevoflurane with cyclodextrin after removal of the precipitated complex) is introduced into headspace vials (19.5 ml) together with 200 µl of DMF.

Example 1

This example describes the preparation of an α-cyclodextrin (α-CD) complex of sevoflurane.

In a round-bottom flask, with continuous stirring at room temperature, 45.25 g (0.0465 mol) of α-CD are dissolved in 500 ml of water. After complete dissolution of the α-CD, 6 ml (0.0465 mol) of sevoflurane were added to the solution at room temperature. A white precipitate precipitated out and was cooled to 5 to 10° C. with ice-water. The mixture was stirred at this temperature for 4 h, then the bottle was stored in a refrigerator overnight. Subsequently, the precipitated sevoflurane/α-CD complex crystals were filtered off and dried over phosphorus pentoxide under reduced pressure.

Example 2

This example shows the influence of the selection of the suitable cyclodextrin on the formation of the complex. For comparative purposes, β-cyclodextrin (β-CD), hydroxypropyl-β-cyclodextrin (HP-β-CD) and RAMEB were used here. These comparative examples are not in accordance with the invention.

1 ml of an aqueous solution of each of 4 cyclodextrins was prepared. The concentration of the cyclodextrins in this aqueous solution was as follows:

| | |
|---|---|
| α-CD: | 10% by weight |
| β-CD: | 2% by weight |
| HP-β-CD: | 10% by weight |
| RAMEB: | 10% by weight |

Sevoflurane was added to these solutions in a molar ratio of 1:1 based on the molar content of the respective cyclodextrin.

A homogeneous solution was obtained in the case of HP-β-CD and RAMEB; no complex was precipitated.

α-CD and β-CD formed a white precipitate.

In a next step, 100 ml of aqueous solution of each of α-CD (9.05% by weight) and β-CD (1.78% by weight) were prepared. Again, sevoflurane was added in a molar ratio of 1:1. The further recovery from precipitated white precipitate was effected as described in example 1.

The sevoflurane content of the precipitated complex was determined by gas chromatography. The results are reported in table 1 below.

| | α-CD | β-CD |
|---|---|---|
| CD concentration (%) | 9.05 | 1.78 |
| Moist mass (g) | 10.00 | 0.97 |
| Dried mass (g) | 6.57 | 0.83 |
| Yield (%) | 72.6 | 46.6 |
| Sevoflurane content (%) | 9.2 | 1.8 |
| Molar sevoflurane/CD ratio | 1:1.8 | 1:8.6 |

The table shows that α-CD is suitable for formation of a complex with a high sevoflurane content, while β-CD enables only comparatively low contents of sevoflurane in the complex.

Example 3

In this example, the production conditions for production of a sevoflurane complex with α-CD were varied. The results are shown in table 2 below.

| | 3.1 | 3.2 | 3.3 | 3.4 |
|---|---|---|---|---|
| α-CD (g) | 9.11 | 9.08 | 9.06 | 9.09 |
| Sevoflurane (cm$^3$) | 1.2 | 1.2 | 0.6 | 1.2 |
| Molar sevoflurane/CD ratio | 1:1 | 1:1 | 1:2 | 1:1 |
| Water (cm$^3$) | 14 | 100 | 100 | 40 |
| Product filtered off | | | | |
| Moist mass (g) | 17.36 | 10.66 | 6.78 | 19.14 |
| Dried mass (g) | 9.49 | 5.65 | 3.53 | 9.01 |
| Yield (%) | 86.8 | 51.8 | 35.4 | 82.5 |
| Sevoflurane content (%) | 3.5 | 10.0 | 11.3 | 5.7 |
| Molar sevoflurane/CD ratio | 1:5.7 | 1:1.9 | 1:1.7 | 1:3.0 |

In example 3.1, a comparatively small amount of water was used, and so it was not possible to completely dissolve α-CD. It can be seen that the sevoflurane content of the complex is reduced under these production conditions.

Example 3.4 shows a further experiment with a low water content. It can be seen that a high yield is likewise obtained here, but the sevoflurane content of the complex is lower at 5.7% by weight than in example 1.

Examples 2.2 and 2.3 work with a higher water content. The molar sevoflurane/α-cyclodextrin ratio in the starting solution is set at different levels here (1:1 in example 3.2, 1:2 in example 3.3). In both cases, a high sevoflurane content in the complex is obtained. The use of sevoflurane in a distinct excess compared to the molar ratio in the complex (example 2.2) increases the yield, as evident from the table.

Example 4

It was found from the above experiments that a good yield and a high sevoflurane content in the complex are achieved when a 9% α-cyclodextrin solution in water is prepared and the molar ratio of sevoflurane added to α-CD dissolved is 1:1. Table 3 below shows that the production of the complex is reliably reproducible under these conditions. In the three experiments substantially identical or comparable results were obtained.

| | 4.1 | 4.2 | 4.3 |
|---|---|---|---|
| α-CD (g) | 45.25 | 45.25 | 45.25 |
| Sevoflurane (cm$^3$) | 6.0 | 6.0 | 6.0 |
| Molar sevoflurane/CD ratio | 1:1 | 1:1 | 1:1 |
| Water (cm$^3$) | 500 | 500 | 500 |

-continued

|  | 4.1 | 4.2 | 4.3 |
|---|---|---|---|
| Product filtered off | | | |
| Moist mass (g) | 36.22 | 34.96 | 39.74 |
| Dried mass (g) | 25.07 | 23.36 | 21.22 |
| Yield (%) | 46.1 | 43.0 | 39.0 |
| Water content (%) | 9.38 | 10.95 | 8.93 |
| Sevoflurane content (%) | 9.4 | 8.6 | 8.6 |
| Molar sevoflurane/CD ratio | 1:1.8 | 1:1.9 | 1:2.0 |

The invention claimed is:

1. A complex formed for α-cyclodextrin and a flurane, wherein said complex is characterized by having a flurane content of at least 3% by weight in the total weight of the complex.

2. The complex as claimed in claim 1, wherein said flurane content is at least 5% by weight.

3. The complex of claim 1, wherein said flurane content is at least 7% by weight.

4. The complex of claim 1, wherein said flurane content is at least 8% by weight.

5. The complex of claim 1, wherein said flurane content is 8 to 12% by weight.

6. The complex of claim 1, wherein said flurane is selected from the group consisting of sevoflurane, enflurane, isoflurane, desflurane and methoxyflurane.

7. The complex of claim 1, wherein said complex has a water content of 5 to 15% by weight.

8. The complex of claim 7, wherein said complex has a water content of 7 to 13% by weight.

9. A medicament composition comprising the complex of claim 1.

10. An anesthetic composition formulated for oral and/or intravenous administration, wherein said composition comprises the complex of claim 1.

11. A process for producing the complex of claim 1, comprising:
   a. preparing an aqueous solution of α-cyclodextrin, wherein the concentration of α-cyclodextrin in said aqueous solution is 5 to 30% by weight,
   b. adding flurane to said aqueous solution to produce a mixture, wherein the flurane is added in a molar ratio relative to α-cyclodextrin of 1:0.5 to 1:2,
   c. collecting a precipitate from said mixture, wherein said precipitate comprises said complex.

12. The process of claim 11, wherein the concentration of α-cyclodextrin in said aqueous solution prepared in step a) is 5 to 20% by weight.

13. The process of claim 11, wherein the concentration of α-cyclodextrin in said aqueous solution prepared in step a) is 5 to 15% by weight.

14. The process of claim 11, wherein the flurane is added in step b) in a molar ratio relative to α-cyclodextrin of 1:0.8 to 1:1.2.

15. The process of claim 11, wherein the flurane is added in step b) at room temperature.

16. The process of claim 11, wherein the addition of the flurane is followed by cooling said mixture.

17. The process of claim 16, wherein said cooling of said mixture is to a temperature between about 5 and 10° C., inclusive.

* * * * *